(12) United States Patent
Buan et al.

(10) Patent No.: US 12,097,095 B2
(45) Date of Patent: Sep. 24, 2024

(54) METHOD AND APPARATUS FOR PROVIDING NEGATIVE PRESSURE TO A NEGATIVE PRESSURE WOUND THERAPY BANDAGE

(71) Applicant: Smith & Nephew, Inc., Memphis, TN (US)

(72) Inventors: John Buan, Maple Grove, MN (US); Richard Willems, Big Lake, MN (US)

(73) Assignee: Smith & Nephew, Inc., Memphis, TN (US)

( * ) Notice: Subject to any disclaimer, the term of this patent is extended or adjusted under 35 U.S.C. 154(b) by 258 days.

(21) Appl. No.: 17/555,195

(22) Filed: Dec. 17, 2021

(65) Prior Publication Data
US 2022/0105255 A1    Apr. 7, 2022

Related U.S. Application Data

(63) Continuation of application No. 16/234,241, filed on Dec. 27, 2018, now abandoned, which is a continuation of application No. 14/737,387, filed on Jun. 11, 2015, now Pat. No. 10,300,178, which is a
(Continued)

(51) Int. Cl.
*A61M 1/00*    (2006.01)
*A61F 13/05*    (2024.01)
*A61F 13/00*    (2006.01)

(52) U.S. Cl.
CPC .............. *A61F 13/05* (2024.01); *A61M 1/74* (2021.05); *A61M 1/75* (2021.05); *A61M 1/96* (2021.05); *A61F 2013/00174* (2013.01); *A61F 2013/00536* (2013.01); *A61M 2205/33* (2013.01); *A61M 2210/04* (2013.01)

(58) Field of Classification Search
CPC ...... A61F 13/00068; A61F 2013/00174; A61F 2013/00536; A61M 1/74; A61M 1/75; A61M 1/96; A61M 2205/33; A61M 2210/04
See application file for complete search history.

(56) References Cited

U.S. PATENT DOCUMENTS

| 695,270 A | 3/1902 | Beringer |
| 1,480,562 A | 1/1924 | Hugo et al. |
| 2,280,915 A | 4/1942 | Johnson |

(Continued)

FOREIGN PATENT DOCUMENTS

| CA | 2198243 A1 | 2/1996 |
| CA | 2367460 A1 | 10/2000 |

(Continued)

OTHER PUBLICATIONS

Achterberg V., et al., "Hydroactive Dressings and Serum Proteins: An In Vitro Study," Journal of Wound Care, vol. 5 (2), Feb. 1996, pp. 79-82.

(Continued)

*Primary Examiner* — Kai H Weng
(74) *Attorney, Agent, or Firm* — Knobbe, Martens, Olson & Bear, LLP (57) ABSTRACT

A method for providing a negative pressure wherein a pump is cycled on and off to achieve a target negative pressure, which is set slightly lower than the therapeutic negative pressure. A device determines the actual pressure by averaging samples which may occur at a different rate than the pump cycle.

14 Claims, 3 Drawing Sheets

Related U.S. Application Data continuation of application No. 13/299,783, filed on Nov. 18, 2011, now Pat. No. 9,067,003.

(60) Provisional application No. 61/490,118, filed on May 26, 2011.

(56) References Cited

U.S. PATENT DOCUMENTS

| | | |
|---|---|---|
| 2,367,690 A | 1/1945 | Purdy |
| 2,568,933 A | 9/1951 | Robbins |
| 2,632,443 A | 3/1953 | Lesher |
| 2,682,873 A | 7/1954 | Idnis et al. |
| 3,367,332 A | 2/1968 | Groves |
| 3,486,504 A | 12/1969 | Austin, Jr. et al. |
| 3,572,340 A | 3/1971 | Lloyd et al. |
| 3,610,238 A | 10/1971 | Rich, Jr. |
| 3,874,387 A | 4/1975 | Barbieri |
| 3,993,080 A | 11/1976 | Loseff |
| RE29,319 E | 7/1977 | Nordby et al. |
| 4,062,012 A | 12/1977 | Colbert et al. |
| 4,102,342 A | 7/1978 | Akiyama et al. |
| 4,112,947 A | 9/1978 | Nehring |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,250,882 A | 2/1981 | Adair |
| 4,316,466 A | 2/1982 | Babb |
| 4,382,441 A | 5/1983 | Svedman |
| 4,465,485 A | 8/1984 | Kashmer et al. |
| 4,468,227 A | 8/1984 | Jensen |
| 4,525,166 A | 6/1985 | Leclerc |
| 4,534,356 A | 8/1985 | Papadakis |
| 4,551,141 A | 11/1985 | McNeil |
| 4,573,965 A | 3/1986 | Russo |
| 4,608,041 A | 8/1986 | Nielsen |
| 4,643,641 A | 2/1987 | Clausen et al. |
| 4,655,766 A | 4/1987 | Theeuwes et al. |
| 4,681,562 A | 7/1987 | Beck et al. |
| 4,710,165 A | 12/1987 | McNeil et al. |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,820,284 A | 4/1989 | Hauri |
| 4,921,488 A | 5/1990 | Maitz et al. |
| 4,936,834 A | 6/1990 | Beck et al. |
| 4,950,483 A | 8/1990 | Ksander et al. |
| 4,969,880 A | 11/1990 | Zamierowski |
| 4,972,829 A | 11/1990 | Knerr |
| 4,979,944 A | 12/1990 | Luzsicza |
| 4,994,022 A | 2/1991 | Steffler et al. |
| 5,055,198 A | 10/1991 | Shettigar |
| 5,056,510 A | 10/1991 | Gilman |
| 5,073,172 A | 12/1991 | Fell |
| 5,100,396 A | 3/1992 | Zamierowski |
| 5,127,388 A | 7/1992 | Cicalese et al. |
| 5,149,331 A | 9/1992 | Ferdman et al. |
| 5,152,757 A | 10/1992 | Eriksson |
| 5,167,613 A | 12/1992 | Karami et al. |
| 5,176,663 A | 1/1993 | Svedman et al. |
| 5,215,519 A | 6/1993 | Shettigar |
| 5,222,714 A | 6/1993 | Morinigo et al. |
| 5,261,893 A | 11/1993 | Zamierowski |
| 5,266,928 A | 11/1993 | Johnson |
| 5,279,608 A | 1/1994 | Cherif Cheikh |
| 5,291,822 A | 3/1994 | Alsobrooks et al. |
| 5,328,614 A | 7/1994 | Matsumura |
| 5,349,896 A | 9/1994 | Delaney, III et al. |
| 5,358,494 A | 10/1994 | Svedman |
| 5,380,280 A | 1/1995 | Peterson |
| 5,417,743 A | 5/1995 | Dauber |
| 5,437,651 A | 8/1995 | Todd et al. |
| 5,445,604 A | 8/1995 | Lang |
| 5,449,003 A | 9/1995 | Sugimura |
| 5,449,347 A | 9/1995 | Preen et al. |
| 5,466,229 A | 11/1995 | Elson et al. |
| 5,489,280 A | 2/1996 | Russell |
| 5,498,338 A | 3/1996 | Kruger et al. |
| 5,527,293 A | 6/1996 | Zamierowski |
| 5,549,584 A | 8/1996 | Gross |
| 5,562,107 A | 10/1996 | Lavender et al. |
| 5,616,121 A | 4/1997 | Mckay |
| 5,634,391 A | 6/1997 | Eady |
| 5,636,643 A | 6/1997 | Argenta et al. |
| 5,643,189 A | 7/1997 | Masini |
| 5,645,081 A | 7/1997 | Argenta et al. |
| 5,676,525 A | 10/1997 | Berner et al. |
| 5,678,564 A | 10/1997 | Lawrence et al. |
| 5,687,633 A | 11/1997 | Eady |
| 5,693,013 A | 12/1997 | Geuder |
| 5,730,587 A | 3/1998 | Snyder et al. |
| 5,733,337 A | 3/1998 | Carr, Jr. et al. |
| 5,743,170 A | 4/1998 | Pascual et al. |
| 5,759,570 A | 6/1998 | Arnold |
| 5,769,608 A | 6/1998 | Seale |
| 5,785,508 A | 7/1998 | Bolt |
| 5,785,688 A | 7/1998 | Joshi et al. |
| 5,830,496 A | 11/1998 | Freeman |
| 5,833,646 A | 11/1998 | Masini |
| 5,843,011 A | 12/1998 | Lucas |
| 5,857,502 A | 1/1999 | Buchalter |
| 5,863,184 A | 1/1999 | Juterbock et al. |
| 5,868,933 A | 2/1999 | Patrick et al. |
| 5,876,611 A | 3/1999 | Shettigar |
| 5,897,296 A | 4/1999 | Yamamoto et al. |
| 5,950,523 A | 9/1999 | Reynolds |
| 5,964,723 A | 10/1999 | Augustine |
| 6,068,588 A | 5/2000 | Goldowsky |
| 6,071,267 A | 6/2000 | Zamierowski |
| 6,080,685 A | 6/2000 | Eady |
| 6,102,680 A | 8/2000 | Fraser et al. |
| 6,103,951 A | 8/2000 | Freeman |
| 6,110,197 A | 8/2000 | Augustine et al. |
| 6,135,116 A | 10/2000 | Vogel et al. |
| 6,138,550 A | 10/2000 | Fingar, Jr. et al. |
| D434,150 S | 11/2000 | Tumey et al. |
| 6,142,982 A | 11/2000 | Hunt et al. |
| 6,145,430 A | 11/2000 | Able et al. |
| 6,158,327 A | 12/2000 | Huss |
| 6,162,194 A | 12/2000 | Shipp |
| 6,168,800 B1 | 1/2001 | Dobos et al. |
| 6,176,307 B1 | 1/2001 | Danos et al. |
| 6,225,523 B1 | 5/2001 | Masini |
| 6,227,825 B1 | 5/2001 | Vay |
| 6,230,609 B1 | 5/2001 | Bender et al. |
| 6,231,310 B1 | 5/2001 | Tojo et al. |
| 6,249,198 B1 | 6/2001 | Clark et al. |
| 6,254,567 B1 | 7/2001 | Treu et al. |
| 6,255,552 B1 | 7/2001 | Cummings et al. |
| 6,261,283 B1 | 7/2001 | Morgan et al. |
| 6,287,521 B1 | 9/2001 | Quay et al. |
| 6,323,568 B1 | 11/2001 | Zabar |
| 6,327,960 B1 | 12/2001 | Heimueller et al. |
| 6,343,539 B1 | 2/2002 | Du |
| 6,345,623 B1 | 2/2002 | Heaton et al. |
| 6,383,163 B1 | 5/2002 | Kelly et al. |
| 6,398,767 B1 | 6/2002 | Fleischmann |
| 6,402,724 B1 | 6/2002 | Smith et al. |
| 6,413,057 B1 | 7/2002 | Hong et al. |
| 6,450,773 B1 | 9/2002 | Upton |
| 6,458,109 B1 | 10/2002 | Henley et al. |
| 6,465,708 B1 | 10/2002 | Augustine |
| 6,471,685 B1 | 10/2002 | Johnson |
| 6,471,982 B1 | 10/2002 | Lydon et al. |
| 6,482,491 B1 | 11/2002 | Samuelsen et al. |
| 6,491,684 B1 | 12/2002 | Joshi et al. |
| 6,540,490 B1 | 4/2003 | Lilie |
| 6,553,998 B2 | 4/2003 | Heaton et al. |
| 6,589,028 B1 | 7/2003 | Eckerbom et al. |
| 6,599,262 B1 | 7/2003 | Masini |
| 6,638,035 B1 | 10/2003 | Puff |
| 6,648,862 B2 | 11/2003 | Watson |

(56) References Cited

U.S. PATENT DOCUMENTS

| | | |
|---|---|---|
| 6,655,257 B1 | 12/2003 | Meyer |
| 6,673,028 B1 | 1/2004 | Argenta et al. |
| 6,673,036 B1 | 1/2004 | Britto |
| 6,676,610 B2 | 1/2004 | Morton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,756,903 B2 | 6/2004 | Omry et al. |
| 6,764,462 B2 | 7/2004 | Risk, Jr. et al. |
| 6,767,334 B1 | 7/2004 | Randolph |
| 6,814,079 B2 | 11/2004 | Heaton et al. |
| 6,823,905 B1 | 11/2004 | Smith et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,977,323 B1 | 12/2005 | Swenson |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,041,057 B1 | 5/2006 | Faupel et al. |
| 7,067,709 B2 | 6/2006 | Murata et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,118,545 B2 | 10/2006 | Boyde |
| 7,128,735 B2 | 10/2006 | Weston |
| 7,151,348 B1 | 12/2006 | Ueda et al. |
| 7,195,624 B2 | 3/2007 | Lockwood et al. |
| 7,214,202 B1 | 5/2007 | Vogel et al. |
| 7,216,651 B2 | 5/2007 | Argenta et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,447,327 B2 | 11/2008 | Kitamura et al. |
| 7,494,482 B2 | 2/2009 | Orgill et al. |
| 7,503,910 B2 | 3/2009 | Adahan |
| 7,524,315 B2 | 4/2009 | Blott et al. |
| 7,534,240 B1 | 5/2009 | Johnson |
| 7,534,927 B2 | 5/2009 | Lockwood et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,645,253 B2 | 1/2010 | Gura et al. |
| 7,645,269 B2 | 1/2010 | Zamierowski |
| 7,670,323 B2 | 3/2010 | Hunt et al. |
| 7,678,090 B2 | 3/2010 | Risk, Jr. et al. |
| 7,699,823 B2 | 4/2010 | Haggstrom et al. |
| 7,699,830 B2 | 4/2010 | Martin |
| 7,708,724 B2 | 5/2010 | Weston |
| 7,717,313 B2 | 5/2010 | Criscuolo et al. |
| 7,753,894 B2 | 7/2010 | Blott et al. |
| 7,758,555 B2 | 7/2010 | Kelch et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,811,269 B2 | 10/2010 | Boynton et al. |
| 7,815,616 B2 | 10/2010 | Boehringer et al. |
| 7,825,289 B2 | 11/2010 | Vess |
| 7,828,782 B2 | 11/2010 | Suzuki |
| 7,838,717 B2 | 11/2010 | Haggstrom et al. |
| 7,846,141 B2 | 12/2010 | Weston |
| 7,862,339 B2 | 1/2011 | Mulligan |
| 7,883,494 B2 | 2/2011 | Martin |
| 7,909,805 B2 | 3/2011 | Weston |
| 7,927,319 B2 | 4/2011 | Lawhorn |
| 7,959,624 B2 | 6/2011 | Riesinger |
| 7,964,766 B2 | 6/2011 | Blott et al. |
| 7,976,519 B2 | 7/2011 | Bubb et al. |
| 7,998,125 B2 | 8/2011 | Weston |
| 8,025,052 B2 | 9/2011 | Matthews et al. |
| 8,062,272 B2 | 11/2011 | Weston |
| 8,062,273 B2 | 11/2011 | Weston |
| 8,080,702 B2 | 12/2011 | Blott et al. |
| 8,100,887 B2 | 1/2012 | Weston et al. |
| 8,105,295 B2 | 1/2012 | Blott et al. |
| 8,118,794 B2 | 2/2012 | Weston |
| 8,128,615 B2 | 3/2012 | Blott et al. |
| 8,152,785 B2 | 4/2012 | Vitaris |
| 8,162,907 B2 | 4/2012 | Heagle |
| 8,162,909 B2 | 4/2012 | Blott et al. |
| 8,167,869 B2 | 5/2012 | Wudyka |
| 8,202,262 B2 | 6/2012 | Lina et al. |
| 8,235,955 B2 | 8/2012 | Blott et al. |
| 8,241,015 B2 | 8/2012 | Lillie et al. |
| 8,241,018 B2 | 8/2012 | Harr |
| 8,267,918 B2 | 9/2012 | Johnson et al. |
| 8,282,611 B2 | 10/2012 | Weston |
| 8,294,586 B2 | 10/2012 | Pidgeon et al. |
| 8,303,552 B2 | 11/2012 | Weston |
| 8,308,714 B2 | 11/2012 | Weston et al. |
| 8,317,774 B2 | 11/2012 | Adahan |
| 8,323,264 B2 | 12/2012 | Weston et al. |
| 8,353,857 B2 | 1/2013 | Rosenberg |
| 8,366,690 B2 | 2/2013 | Locke et al. |
| 8,366,692 B2 | 2/2013 | Weston et al. |
| 8,377,016 B2 | 2/2013 | Argenta et al. |
| 8,398,614 B2 | 3/2013 | Blott et al. |
| D679,819 S | 4/2013 | Peron |
| D679,820 S | 4/2013 | Peron |
| 8,409,170 B2 | 4/2013 | Locke et al. |
| 8,444,392 B2 | 5/2013 | Turner et al. |
| 8,449,509 B2 | 5/2013 | Weston |
| 8,460,255 B2 | 6/2013 | Joshi et al. |
| 8,494,349 B2 | 7/2013 | Gordon |
| 8,540,688 B2 | 9/2013 | Eckstein et al. |
| 8,617,129 B2 | 12/2013 | Hartwell |
| 8,622,981 B2 | 1/2014 | Hartwell et al. |
| 8,641,693 B2 | 2/2014 | Locke et al. |
| 8,663,198 B2 | 3/2014 | Buan et al. |
| 8,663,200 B2 | 3/2014 | Weston et al. |
| 8,715,256 B2 | 5/2014 | Greener |
| 8,734,425 B2 | 5/2014 | Nicolini |
| 8,764,732 B2 | 7/2014 | Hartwell |
| 8,785,059 B2 | 7/2014 | Hartwell |
| 8,795,243 B2 | 8/2014 | Weston |
| 8,808,259 B2 | 8/2014 | Walton et al. |
| 8,808,274 B2 | 8/2014 | Hartwell |
| 8,814,841 B2 | 8/2014 | Hartwell |
| 8,827,983 B2 | 9/2014 | Braga et al. |
| 8,834,451 B2 | 9/2014 | Blott et al. |
| 8,905,985 B2 | 12/2014 | Allen et al. |
| 8,945,074 B2 | 2/2015 | Buan et al. |
| 8,951,235 B2 | 2/2015 | Allen et al. |
| 9,067,003 B2 | 6/2015 | Buan et al. |
| 9,084,845 B2 | 7/2015 | Adie et al. |
| 9,199,011 B2 | 12/2015 | Locke et al. |
| 9,506,463 B2 | 11/2016 | Locke et al. |
| 9,518,575 B2 | 12/2016 | Felber |
| 9,526,817 B2 | 12/2016 | Blott et al. |
| 2001/0001278 A1 | 5/2001 | Drevet |
| 2001/0016205 A1 | 8/2001 | Shimizu |
| 2001/0029956 A1 | 10/2001 | Argenta et al. |
| 2001/0033795 A1 | 10/2001 | Humpheries |
| 2001/0034499 A1 | 10/2001 | Sessions et al. |
| 2001/0043870 A1 | 11/2001 | Song |
| 2002/0026946 A1 | 3/2002 | McKay |
| 2002/0065494 A1 | 5/2002 | Lockwood et al. |
| 2002/0068913 A1 | 6/2002 | Fleischmann |

(56) References Cited

U.S. PATENT DOCUMENTS

| | | |
|---|---|---|
| 2002/0115952 A1 | 8/2002 | Johnson et al. |
| 2002/0120185 A1 | 8/2002 | Johnson |
| 2002/0122732 A1 | 9/2002 | Oh et al. |
| 2002/0143286 A1 | 10/2002 | Tumey |
| 2002/0150720 A1 | 10/2002 | Howard et al. |
| 2002/0161346 A1 | 10/2002 | Lockwood et al. |
| 2002/0164255 A1 | 11/2002 | Burr et al. |
| 2002/0183702 A1 | 12/2002 | Henley et al. |
| 2002/0198503 A1 | 12/2002 | Risk, Jr. et al. |
| 2002/0198504 A1 | 12/2002 | Risk, Jr. et al. |
| 2003/0014022 A1 | 1/2003 | Lockwood et al. |
| 2003/0014025 A1 | 1/2003 | Allen et al. |
| 2003/0021775 A1 | 1/2003 | Freeman |
| 2003/0035743 A1 | 2/2003 | Lee et al. |
| 2003/0040687 A1 | 2/2003 | Boynton et al. |
| 2003/0050594 A1 | 3/2003 | Zamierowski |
| 2003/0088202 A1 | 5/2003 | Gilman |
| 2003/0095879 A1 | 5/2003 | Oh et al. |
| 2003/0097086 A1 | 5/2003 | Gura |
| 2003/0099558 A1 | 5/2003 | Chang |
| 2003/0108430 A1 | 6/2003 | Yoshida et al. |
| 2003/0108587 A1 | 6/2003 | Orgill et al. |
| 2003/0110939 A1 | 6/2003 | Able et al. |
| 2003/0125649 A1 | 7/2003 | McIntosh et al. |
| 2003/0133812 A1 | 7/2003 | Puff et al. |
| 2003/0144619 A1 | 7/2003 | Augustine |
| 2003/0161735 A1 | 8/2003 | Kim et al. |
| 2003/0171675 A1 | 9/2003 | Rosenberg |
| 2003/0175125 A1 | 9/2003 | Kwon et al. |
| 2003/0175135 A1 | 9/2003 | Heo et al. |
| 2003/0175798 A1 | 9/2003 | Raees et al. |
| 2003/0208149 A1 | 11/2003 | Coffey |
| 2003/0212357 A1 | 11/2003 | Pace |
| 2003/0212431 A1 | 11/2003 | Brady et al. |
| 2003/0225347 A1 | 12/2003 | Argenta et al. |
| 2003/0230191 A1 | 12/2003 | Ohrle et al. |
| 2004/0005222 A1 | 1/2004 | Yoshida et al. |
| 2004/0019342 A1 | 1/2004 | Nagasuna et al. |
| 2004/0030304 A1 | 2/2004 | Hunt et al. |
| 2004/0039391 A1 | 2/2004 | Argenta et al. |
| 2004/0039415 A1 | 2/2004 | Zamierowski |
| 2004/0054338 A1 | 3/2004 | Bybordi et al. |
| 2004/0064132 A1 | 4/2004 | Boehringer et al. |
| 2004/0066097 A1 | 4/2004 | Kobayashi et al. |
| 2004/0071568 A1 | 4/2004 | Hyeon |
| 2004/0071572 A1 | 4/2004 | Greter |
| 2004/0115076 A1 | 6/2004 | Lilie et al. |
| 2004/0118460 A1 | 6/2004 | Stinson |
| 2004/0122434 A1 | 6/2004 | Argenta et al. |
| 2004/0126250 A1 | 7/2004 | Tsuchiya et al. |
| 2004/0127834 A1 | 7/2004 | Sigurjonsson et al. |
| 2004/0127862 A1 | 7/2004 | Bubb et al. |
| 2004/0127863 A1 | 7/2004 | Bubb et al. |
| 2004/0156730 A1 | 8/2004 | Lilie et al. |
| 2004/0163713 A1 | 8/2004 | Schulze et al. |
| 2004/0167482 A1 | 8/2004 | Watson |
| 2004/0182237 A1 | 9/2004 | Headley et al. |
| 2004/0189103 A1 | 9/2004 | Duncan et al. |
| 2004/0225208 A1 | 11/2004 | Johnson |
| 2004/0241214 A1 | 12/2004 | Kirkwood et al. |
| 2004/0249353 A1 | 12/2004 | Risks, Jr. et al. |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0028828 A1 | 2/2005 | Heaton et al. |
| 2005/0031470 A1 | 2/2005 | Lee |
| 2005/0033214 A1 | 2/2005 | Cantor |
| 2005/0058694 A1 | 3/2005 | Nielsen |
| 2005/0070835 A1 | 3/2005 | Joshi |
| 2005/0080372 A1 | 4/2005 | Nielsen et al. |
| 2005/0090787 A1 | 4/2005 | Risk et al. |
| 2005/0098031 A1 | 5/2005 | Yoon et al. |
| 2005/0110190 A1 | 5/2005 | Giardini et al. |
| 2005/0111987 A1 | 5/2005 | Yoo et al. |
| 2005/0123422 A1 | 6/2005 | Lilie |
| 2005/0124966 A1 | 6/2005 | Karpowicz et al. |
| 2005/0129540 A1 | 6/2005 | Puff |
| 2005/0135946 A1 | 6/2005 | Kang et al. |
| 2005/0142007 A1 | 6/2005 | Lee et al. |
| 2005/0142008 A1 | 6/2005 | Jung et al. |
| 2005/0148913 A1 | 7/2005 | Weston |
| 2005/0155657 A1 | 7/2005 | Kach et al. |
| 2005/0163635 A1 | 7/2005 | Berwanger et al. |
| 2005/0209560 A1 | 9/2005 | Boukhny et al. |
| 2005/0222527 A1 | 10/2005 | Miller et al. |
| 2005/0251117 A1 | 11/2005 | Anderson et al. |
| 2005/0261643 A1 | 11/2005 | Bybordi et al. |
| 2005/0267402 A1 | 12/2005 | Stewart et al. |
| 2005/0271526 A1 | 12/2005 | Chang et al. |
| 2005/0272142 A1 | 12/2005 | Horita |
| 2005/0276706 A1 | 12/2005 | Radue |
| 2006/0015087 A1 | 1/2006 | Risk et al. |
| 2006/0017332 A1 | 1/2006 | Kang et al. |
| 2006/0018771 A1 | 1/2006 | Song et al. |
| 2006/0019144 A1 | 1/2006 | Hidaka et al. |
| 2006/0024181 A1 | 2/2006 | Kim |
| 2006/0025727 A1 | 2/2006 | Boehringer et al. |
| 2006/0029650 A1 | 2/2006 | Coffey |
| 2006/0029675 A1 | 2/2006 | Ginther |
| 2006/0039806 A1 | 2/2006 | Becker |
| 2006/0041247 A1 | 2/2006 | Petrosenko et al. |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0069365 A1 | 3/2006 | Sperl et al. |
| 2006/0073036 A1 | 4/2006 | Pascual et al. |
| 2006/0079852 A1 | 4/2006 | Bubb et al. |
| 2006/0083623 A1 | 4/2006 | Higgins et al. |
| 2006/0100586 A1 | 5/2006 | Karpowicz et al. |
| 2006/0100594 A1 | 5/2006 | Adams et al. |
| 2006/0110259 A1 | 5/2006 | Puff et al. |
| 2006/0116620 A1 | 6/2006 | Oyaski |
| 2006/0118190 A1 | 6/2006 | Takehana et al. |
| 2006/0122558 A1 | 6/2006 | Sherman et al. |
| 2006/0129137 A1 | 6/2006 | Lockwood et al. |
| 2006/0149170 A1 | 7/2006 | Boynton et al. |
| 2006/0191575 A1 | 8/2006 | Naesje |
| 2006/0192259 A1 | 8/2006 | Silverbrook |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0245947 A1 | 11/2006 | Seto et al. |
| 2006/0251523 A1 | 11/2006 | Lee et al. |
| 2006/0282174 A1 | 12/2006 | Haines |
| 2006/0282175 A1 | 12/2006 | Haines et al. |
| 2006/0287632 A1 | 12/2006 | Sarangapani |
| 2007/0005028 A1 | 1/2007 | Risk et al. |
| 2007/0010797 A1 | 1/2007 | Nishtala et al. |
| 2007/0032741 A1 | 2/2007 | Hibner et al. |
| 2007/0032762 A1 | 2/2007 | Vogel |
| 2007/0038172 A1 | 2/2007 | Zamierowski |
| 2007/0041856 A1 | 2/2007 | Hansen et al. |
| 2007/0055209 A1 | 3/2007 | Patel et al. |
| 2007/0078444 A1 | 4/2007 | Larsson |
| 2007/0091614 A1 | 4/2007 | Kaisser et al. |
| 2007/0118096 A1 | 5/2007 | Smith et al. |
| 2007/0141128 A1 | 6/2007 | Blott et al. |
| 2007/0167884 A1 | 7/2007 | Mangrum et al. |
| 2007/0179460 A1 | 8/2007 | Adahan |
| 2007/0185426 A1 | 8/2007 | Ambrosio et al. |
| 2007/0185463 A1 | 8/2007 | Mulligan |
| 2007/0196214 A1 | 8/2007 | Bocchiola |
| 2007/0219532 A1 | 9/2007 | Karpowicz et al. |
| 2007/0239139 A1 | 10/2007 | Weston et al. |
| 2007/0256428 A1 | 11/2007 | Unger et al. |
| 2007/0260226 A1 | 11/2007 | Jaeb et al. |
| 2007/0265585 A1 | 11/2007 | Joshi et al. |
| 2007/0265586 A1 | 11/2007 | Joshi et al. |
| 2007/0282283 A1 | 12/2007 | Kaern et al. |
| 2007/0295201 A1 | 12/2007 | Dadd |
| 2008/0004549 A1 | 1/2008 | Anderson et al. |
| 2008/0004559 A1 | 1/2008 | Riesinger |

(56) References Cited

U.S. PATENT DOCUMENTS

| | | |
|---|---|---|
| 2008/0015526 A1 | 1/2008 | Reiner et al. |
| 2008/0020178 A1 | 1/2008 | Ohrle et al. |
| 2008/0039759 A1 | 2/2008 | Holm et al. |
| 2008/0051708 A1 | 2/2008 | Kumar et al. |
| 2008/0077091 A1 | 3/2008 | Mulligan |
| 2008/0082040 A1 | 4/2008 | Kubler et al. |
| 2008/0082059 A1 | 4/2008 | Fink et al. |
| 2008/0094753 A1 | 4/2008 | Brodkin et al. |
| 2008/0108977 A1 | 5/2008 | Heaton et al. |
| 2008/0110336 A1 | 5/2008 | Cresswell et al. |
| 2008/0119802 A1 | 5/2008 | Riesinger |
| 2008/0125697 A1 | 5/2008 | Gao |
| 2008/0125698 A1 | 5/2008 | Gerg et al. |
| 2008/0167593 A1 | 7/2008 | Fleischmann |
| 2008/0183119 A1 | 7/2008 | Joshi |
| 2008/0188820 A1 | 8/2008 | Joshi |
| 2008/0208147 A1 | 8/2008 | Argenta et al. |
| 2008/0211435 A1 | 9/2008 | Imagawa |
| 2008/0223378 A1 | 9/2008 | Henderson et al. |
| 2008/0240942 A1 | 10/2008 | Heinrich et al. |
| 2008/0260551 A1 | 10/2008 | Simmons |
| 2008/0269651 A1 | 10/2008 | Warlick et al. |
| 2008/0281281 A1 | 11/2008 | Meyer et al. |
| 2008/0306407 A1 | 12/2008 | Taylor |
| 2008/0306456 A1 | 12/2008 | Riesinger |
| 2008/0310980 A1 | 12/2008 | Ramsdorf et al. |
| 2009/0005746 A1 | 1/2009 | Nielsen et al. |
| 2009/0012441 A1 | 1/2009 | Mulligan |
| 2009/0028733 A1 | 1/2009 | Duwel |
| 2009/0030402 A1 | 1/2009 | Adahan |
| 2009/0036873 A1 | 2/2009 | Nielsen et al. |
| 2009/0053081 A1 | 2/2009 | Griffiths |
| 2009/0054855 A1 | 2/2009 | Blott et al. |
| 2009/0054856 A1 | 2/2009 | Mormino et al. |
| 2009/0069759 A1 | 3/2009 | Blott et al. |
| 2009/0071551 A1 | 3/2009 | Chalich |
| 2009/0081049 A1 | 3/2009 | Tian et al. |
| 2009/0087323 A1 | 4/2009 | Blakey et al. |
| 2009/0105670 A1 | 4/2009 | Bentley et al. |
| 2009/0114293 A1 | 5/2009 | Kanai et al. |
| 2009/0123513 A1 | 5/2009 | Greener |
| 2009/0125004 A1 | 5/2009 | Shen et al. |
| 2009/0129986 A1 | 5/2009 | Wimberger-Friedl et al. |
| 2009/0131888 A1 | 5/2009 | Joshi |
| 2009/0149821 A1 | 6/2009 | Scherson et al. |
| 2009/0166411 A1 | 7/2009 | Kramer et al. |
| 2009/0177135 A1 | 7/2009 | Rogers et al. |
| 2009/0192499 A1 | 7/2009 | Weston et al. |
| 2009/0198201 A1 | 8/2009 | Adahan |
| 2009/0206778 A1 | 8/2009 | Roh et al. |
| 2009/0216170 A1 | 8/2009 | Robinson et al. |
| 2009/0221977 A1 | 9/2009 | Blott et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254053 A1 | 10/2009 | Svensby et al. |
| 2009/0264837 A1 | 10/2009 | Adahan |
| 2009/0270820 A1 | 10/2009 | Johnson et al. |
| 2009/0270833 A1 | 10/2009 | DeBelser et al. |
| 2009/0292264 A1 | 11/2009 | Hudspeth et al. |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299306 A1 | 12/2009 | Buan |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2009/0304534 A1 | 12/2009 | Richter |
| 2009/0306580 A1 | 12/2009 | Blott et al. |
| 2009/0312723 A1 | 12/2009 | Blott et al. |
| 2009/0312728 A1 | 12/2009 | Randolph et al. |
| 2009/0326487 A1 | 12/2009 | Vitaris |
| 2010/0010477 A1 | 1/2010 | Augustine et al. |
| 2010/0036334 A1 | 2/2010 | Heagle et al. |
| 2010/0036367 A1 | 2/2010 | Krohn |
| 2010/0042059 A1 | 2/2010 | Pratt et al. |
| 2010/0042074 A1 | 2/2010 | Weston et al. |
| 2010/0063483 A1 | 3/2010 | Adahan |
| 2010/0063484 A1 | 3/2010 | Heagle |
| 2010/0068820 A1 | 3/2010 | Meathrel et al. |
| 2010/0069858 A1 | 3/2010 | Olson |
| 2010/0069863 A1 | 3/2010 | Olson |
| 2010/0087767 A1 | 4/2010 | McNeil |
| 2010/0098566 A1 | 4/2010 | Kang |
| 2010/0100063 A1 | 4/2010 | Joshi et al. |
| 2010/0100075 A1 | 4/2010 | Weston et al. |
| 2010/0106114 A1 | 4/2010 | Weston et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0126484 A1 | 5/2010 | Skell et al. |
| 2010/0150991 A1 | 6/2010 | Bernstein |
| 2010/0160879 A1 | 6/2010 | Weston |
| 2010/0185163 A1 | 7/2010 | Heagle |
| 2010/0185165 A1 | 7/2010 | Middleton et al. |
| 2010/0191178 A1 | 7/2010 | Ross et al. |
| 2010/0207768 A1 | 8/2010 | Pidgeon et al. |
| 2010/0211030 A1 | 8/2010 | Turner et al. |
| 2010/0244780 A1 | 9/2010 | Turner et al. |
| 2010/0249733 A9 | 9/2010 | Blott et al. |
| 2010/0265649 A1 | 10/2010 | Singh et al. |
| 2010/0268179 A1 | 10/2010 | Kelch et al. |
| 2010/0268198 A1 | 10/2010 | Buan et al. |
| 2010/0274207 A1 | 10/2010 | Weston |
| 2010/0278518 A1 | 11/2010 | Gordon |
| 2010/0280435 A1 | 11/2010 | Raney et al. |
| 2010/0280468 A1 | 11/2010 | Haggstrom et al. |
| 2010/0286635 A1 | 11/2010 | Watson, Jr. |
| 2010/0286638 A1 | 11/2010 | Malhi |
| 2010/0298866 A1 | 11/2010 | Fischvogt |
| 2010/0305490 A1 | 12/2010 | Coulthard et al. |
| 2010/0305524 A1 | 12/2010 | Vess et al. |
| 2010/0312575 A1 | 12/2010 | Witt |
| 2010/0318043 A1 | 12/2010 | Malhi et al. |
| 2010/0318071 A1 | 12/2010 | Wudyka |
| 2010/0324510 A1 | 12/2010 | Andresen et al. |
| 2010/0324516 A1 | 12/2010 | Braga et al. |
| 2010/0325864 A1 | 12/2010 | Briones et al. |
| 2010/0331797 A1 | 12/2010 | Patel et al. |
| 2011/0000069 A1 | 1/2011 | Ramsdorf et al. |
| 2011/0004171 A1 | 1/2011 | Blott et al. |
| 2011/0004172 A1 | 1/2011 | Eckstein et al. |
| 2011/0008179 A1 | 1/2011 | Turner et al. |
| 2011/0009835 A1 | 1/2011 | Blott et al. |
| 2011/0015587 A1 | 1/2011 | Tumey et al. |
| 2011/0015593 A1 | 1/2011 | Svedman et al. |
| 2011/0020588 A1 | 1/2011 | Shimizu et al. |
| 2011/0028918 A1 | 2/2011 | Hartwell |
| 2011/0028921 A1 | 2/2011 | Hartwell et al. |
| 2011/0034892 A1 | 2/2011 | Buan |
| 2011/0038741 A1 | 2/2011 | Lissner et al. |
| 2011/0046584 A1 | 2/2011 | Haggstrom et al. |
| 2011/0054421 A1 | 3/2011 | Hartwell |
| 2011/0054422 A1 | 3/2011 | Locke et al. |
| 2011/0054423 A1 | 3/2011 | Blott et al. |
| 2011/0071415 A1 | 3/2011 | Karwoski et al. |
| 2011/0071483 A1 | 3/2011 | Gordon et al. |
| 2011/0077605 A1 | 3/2011 | Karpowicz et al. |
| 2011/0081267 A1 | 4/2011 | McCrone et al. |
| 2011/0087176 A2 | 4/2011 | Blott et al. |
| 2011/0087178 A2 | 4/2011 | Weston |
| 2011/0087180 A2 | 4/2011 | Weston |
| 2011/0092927 A1 | 4/2011 | Wilkes et al. |
| 2011/0092958 A1 | 4/2011 | Jacobs |
| 2011/0098600 A1 | 4/2011 | Matsumura et al. |
| 2011/0103984 A1 | 5/2011 | Santa |
| 2011/0105963 A1 | 5/2011 | Hu et al. |
| 2011/0106030 A1 | 5/2011 | Scholz |
| 2011/0112492 A1 | 5/2011 | Bharti et al. |

(56) References Cited

U.S. PATENT DOCUMENTS

| | | |
|---|---|---|
| 2011/0118683 A1 | 5/2011 | Weston |
| 2011/0130712 A1 | 6/2011 | Topaz |
| 2011/0171044 A1 | 7/2011 | Flanigan |
| 2011/0172615 A2 | 7/2011 | Greener |
| 2011/0176945 A1 | 7/2011 | Drevet |
| 2011/0176946 A1 | 7/2011 | Drevet |
| 2011/0190735 A1 | 8/2011 | Locke et al. |
| 2011/0202220 A1 | 8/2011 | Seta et al. |
| 2011/0229352 A1 | 9/2011 | Timmer |
| 2011/0230849 A1 | 9/2011 | Coulthard et al. |
| 2011/0236265 A1 | 9/2011 | Hasui et al. |
| 2011/0236277 A1 | 9/2011 | Lee et al. |
| 2011/0251567 A1 | 10/2011 | Blott et al. |
| 2011/0251569 A1 | 10/2011 | Turner et al. |
| 2011/0257572 A1 | 10/2011 | Locke et al. |
| 2011/0275964 A1 | 11/2011 | Greener |
| 2011/0282309 A1 | 11/2011 | Adie et al. |
| 2011/0311379 A1 | 12/2011 | Hale et al. |
| 2012/0000208 A1 | 1/2012 | Hon et al. |
| 2012/0001762 A1 | 1/2012 | Turner et al. |
| 2012/0008817 A1 | 1/2012 | Grinker et al. |
| 2012/0046625 A1 | 2/2012 | Johannison |
| 2012/0053538 A1 | 3/2012 | Blott et al. |
| 2012/0078539 A1 | 3/2012 | Vernon-Harcourt et al. |
| 2012/0109084 A1 | 5/2012 | Blott et al. |
| 2012/0130325 A1 | 5/2012 | Blott et al. |
| 2012/0136325 A1 | 5/2012 | Allen et al. |
| 2012/0157942 A1 | 6/2012 | Weston |
| 2012/0165764 A1 | 6/2012 | Allen et al. |
| 2012/0184930 A1 | 7/2012 | Johannison |
| 2012/0197229 A1 | 8/2012 | Buan et al. |
| 2012/0220960 A1 | 8/2012 | Ruland |
| 2012/0251359 A1 | 10/2012 | Neelakantan et al. |
| 2012/0259299 A1 | 10/2012 | Ryu et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0301341 A1 | 11/2012 | Ota et al. |
| 2012/0302975 A1 | 11/2012 | Buan et al. |
| 2012/0302978 A1 | 11/2012 | Buan et al. |
| 2013/0017110 A1 | 1/2013 | Villagomez et al. |
| 2013/0018338 A1 | 1/2013 | Weston et al. |
| 2013/0042753 A1 | 2/2013 | Becker et al. |
| 2013/0085462 A1 | 4/2013 | Nip et al. |
| 2013/0090613 A1 | 4/2013 | Kelch et al. |
| 2013/0110058 A1 | 5/2013 | Adie et al. |
| 2013/0118622 A1 | 5/2013 | Patzold et al. |
| 2013/0123755 A1 | 5/2013 | Locke et al. |
| 2013/0150813 A1 | 6/2013 | Gordon et al. |
| 2013/0150814 A1 | 6/2013 | Buan |
| 2013/0280113 A1 | 10/2013 | Miranda et al. |
| 2013/0296816 A1 | 11/2013 | Greener |
| 2013/0331823 A1 | 12/2013 | Askem et al. |
| 2013/0340870 A1 | 12/2013 | Ito et al. |
| 2014/0018753 A1 | 1/2014 | Joshi et al. |
| 2014/0088528 A1 | 3/2014 | Hartwell |
| 2014/0100516 A1 | 4/2014 | Hunt et al. |
| 2014/0107599 A1 | 4/2014 | Fink et al. |
| 2014/0121617 A1 | 5/2014 | Locke et al. |
| 2014/0163494 A1 | 6/2014 | Buan et al. |
| 2014/0194835 A1 | 7/2014 | Ehlert |
| 2014/0257212 A1 | 9/2014 | Boynton et al. |
| 2014/0316356 A1 | 10/2014 | Nicolini |
| 2015/0025482 A1 | 1/2015 | Begin et al. |
| 2015/0073363 A1 | 3/2015 | Kelch et al. |
| 2015/0352267 A1 | 12/2015 | Buan et al. |
| 2016/0319957 A1 | 11/2016 | Jaeb et al. |

FOREIGN PATENT DOCUMENTS

| | | |
|---|---|---|
| CA | 2390513 A1 | 5/2001 |
| CA | 2121688 C | 7/2001 |
| CA | 2408305 A1 | 11/2001 |
| CA | 2458285 A1 | 3/2003 |
| CA | 2157772 C | 9/2003 |
| DE | 2809828 A1 | 9/1978 |
| DE | 3935818 A1 | 5/1991 |
| DE | 4012232 A1 | 10/1991 |
| DE | 19844355 A1 | 4/2000 |
| EP | 0020662 B1 | 7/1984 |
| EP | 0208395 A1 | 1/1987 |
| EP | 0355186 A1 | 2/1990 |
| EP | 0759521 A1 | 2/1997 |
| EP | 0775825 A2 | 5/1997 |
| EP | 0793019 A2 | 9/1997 |
| EP | 0809028 A2 | 11/1997 |
| EP | 0777504 B1 | 10/1998 |
| EP | 0898076 A1 | 2/1999 |
| EP | 0782421 B1 | 7/1999 |
| EP | 0708620 B1 | 5/2003 |
| EP | 1088569 B1 | 8/2003 |
| EP | 1449971 A1 | 8/2004 |
| EP | 1440667 B1 | 3/2006 |
| EP | 1284777 B1 | 4/2006 |
| EP | 1171065 B1 | 3/2007 |
| EP | 1476217 B1 | 3/2008 |
| EP | 1897569 A1 | 3/2008 |
| EP | 1121163 B1 | 11/2008 |
| EP | 2098257 A1 | 9/2009 |
| EP | 2161448 A1 | 3/2010 |
| EP | 2216573 A1 | 8/2010 |
| EP | 2302127 A1 | 3/2011 |
| FR | 1163907 A | 10/1958 |
| GB | 114754 A | 4/1918 |
| GB | 641061 A | 8/1950 |
| GB | 1224009 A | 3/1971 |
| GB | 1549756 A | 8/1979 |
| GB | 2195255 A | 4/1988 |
| GB | 2273133 A | 6/1994 |
| GB | 2306580 A | 5/1997 |
| GB | 2378392 A | 2/2003 |
| GB | 2415908 A | 1/2006 |
| GB | 2433298 A | 6/2007 |
| JP | 2002517288 A | 6/2002 |
| JP | 2003165843 A | 6/2003 |
| JP | 2010504805 A | 2/2010 |
| JP | 2010531698 A | 9/2010 |
| SU | 1251912 A1 | 8/1986 |
| WO | WO-8401904 A1 | 5/1984 |
| WO | WO-9011795 A1 | 10/1990 |
| WO | WO-9100718 A1 | 1/1991 |
| WO | WO-9220299 A2 | 11/1992 |
| WO | WO-9421312 A2 | 9/1994 |
| WO | WO-9605873 A1 | 2/1996 |
| WO | WO-9819068 A1 | 5/1998 |
| WO | WO-9901173 A1 | 1/1999 |
| WO | WO-0000743 A1 | 1/2000 |
| WO | WO-0007653 A1 | 2/2000 |
| WO | WO-9964091 A3 | 3/2000 |
| WO | WO-0049968 A2 | 8/2000 |
| WO | WO-0050143 A1 | 8/2000 |
| WO | WO-0056378 A1 | 9/2000 |
| WO | WO-0059424 A1 | 10/2000 |
| WO | WO-0079154 A2 | 12/2000 |
| WO | WO-0119430 A1 | 3/2001 |
| WO | WO-0134223 A1 | 5/2001 |
| WO | WO-0137922 A2 | 5/2001 |
| WO | WO-0185248 A1 | 11/2001 |
| WO | WO-0137922 A3 | 12/2001 |
| WO | WO-0193793 A1 | 12/2001 |
| WO | WO-02083046 A1 | 10/2002 |
| WO | WO-02092783 A2 | 11/2002 |
| WO | WO-03045492 A1 | 6/2003 |
| WO | WO-03057307 A1 | 7/2003 |
| WO | WO-03085810 A1 | 10/2003 |
| WO | WO-03092620 A2 | 11/2003 |
| WO | WO-2004007960 A1 | 1/2004 |
| WO | WO-2004024300 A1 | 3/2004 |
| WO | WO-2004037334 A1 | 5/2004 |
| WO | WO-2004081421 A2 | 9/2004 |
| WO | WO-2005025666 A2 | 3/2005 |
| WO | WO-2005051461 A1 | 6/2005 |
| WO | WO-2005070480 A1 | 8/2005 |
| WO | WO-2005082435 A1 | 9/2005 |

(56) References Cited

FOREIGN PATENT DOCUMENTS

| | | |
|---|---|---|
| WO | WO-2006046060 A2 | 5/2006 |
| WO | WO-2006058801 A1 | 6/2006 |
| WO | WO-2006062276 A1 | 6/2006 |
| WO | WO-2006092333 A1 | 9/2006 |
| WO | WO-2006117207 A1 | 11/2006 |
| WO | WO-2007024230 A1 | 3/2007 |
| WO | WO-2007030601 A2 | 3/2007 |
| WO | WO-2007087811 A1 | 8/2007 |
| WO | WO-2008031418 A2 | 3/2008 |
| WO | WO-2008039223 A1 | 4/2008 |
| WO | WO-2008048481 A2 | 4/2008 |
| WO | WO-2008049029 A2 | 4/2008 |
| WO | WO-2008100440 A1 | 8/2008 |
| WO | WO-2008135997 A2 | 11/2008 |
| WO | WO-2009004291 A2 | 1/2009 |
| WO | WO-2009004371 A1 | 1/2009 |
| WO | WO-2009019415 A2 | 2/2009 |
| WO | WO-2009047524 A2 | 4/2009 |
| WO | WO-2009066105 A1 | 5/2009 |
| WO | WO-2009066106 A1 | 5/2009 |
| WO | WO-2009089390 A2 | 7/2009 |
| WO | WO-2009095170 A2 | 8/2009 |
| WO | WO-2010039481 A1 | 4/2010 |
| WO | WO-2010051418 A2 | 5/2010 |
| WO | WO-2010093753 A1 | 8/2010 |
| WO | WO-2010121186 A1 | 10/2010 |
| WO | WO-2010126444 A1 | 11/2010 |
| WO | WO-2011023275 A1 | 3/2011 |
| WO | WO-2011082461 A1 | 7/2011 |
| WO | WO-2011087871 A2 | 7/2011 |
| WO | WO-2011148188 A1 | 12/2011 |
| WO | WO-2012022484 A1 | 2/2012 |
| WO | WO-2012038724 A1 | 3/2012 |
| WO | WO-2012048179 A2 | 4/2012 |
| WO | WO-2012088572 A1 | 7/2012 |
| WO | WO-2012140180 A1 | 10/2012 |
| WO | WO-2012162370 A1 | 11/2012 |
| WO | WO-2012162382 A1 | 11/2012 |
| WO | WO-2013006932 A1 | 1/2013 |
| WO | WO-2013019017 A1 | 2/2013 |
| WO | WO-2013064852 A1 | 5/2013 |
| WO | WO-2013065423 A1 | 5/2013 |
| WO | WO-2013140255 A1 | 9/2013 |
| WO | WO-2013171585 A2 | 11/2013 |
| WO | WO-2014151930 A2 | 9/2014 |

OTHER PUBLICATIONS

Argenta L C., et al., "Vacuum-Assisted Closure: A New Method for Wound Control and Treatment: Clinical Experience," Annals of Plastic Surgery, vol. 38 (6), Jun. 1997, pp. 563-577.
Arnljots B., et al., "Irrigation Treatment in Split-Thickness Skin Grafting of Intractable Leg Ulcers," Scandinavian Journal of Plastic and Reconstructive Surgery, vol. 19, 1985, pp. 211-213.
Aubrey D.A., et al., "Treatment of the Perineal Wound after Proctectomy by Intermittent Irrigation," Arch. Surg, vol. 119, Oct. 1984, pp. 1141-1144.
Bagautdinov N.A., "Variant of External Vacuum Aspiration in the Treatment of Purulent Diseases of Soft Tissues," in Current Problems in Modern Clinical Surgery, Interdepartmental Collection, 1986, pp. 94-96.
Biblehimer H.L., "Dealing with a Wound that Drains 1.5 Liters a Day," RN, Aug. 1986, pp. 21-23.
Bier A., "Hyperemia as a Therapeutic Agent," UCI CCM Library, 1905, pp. 74-85.
Brubacher L.L., "To Heal a Draining Wound," RN, Mar. 1982, pp. 30-35.
Bucalo B., et al., "Inhibition of Cell Proliferation by Chronic Wound Fluid," Wound Repair and Regeneration, Miami, Jul.-Sep. 1993, pp. 181-186.
Chariker M.E., et al., "Effective Management of Incisional and Cutaneous Fistulae with Closed Suction Wound Drainage," Contemporary Surgery, vol. 34, Jun. 1989, pp. 59-63.

Chintamani et al., "Half Versus Full Vacuum Suction Drainage After Modified Radical Mastectomy for Breast Cancer—a Prospective Randomized Clinical Trial," BMC Cancer, Research Article, vol. 5(11), Jan. 27, 2005, 5 pages.
Communication pursuant to Rule 94(3) EPC for Application No. 04791592.1 dated Feb. 10, 2011, 3 pages.
Communication pursuant to Rule 94(3) EPC for Application No. 04791592.1, mailed Jun. 12, 2008, 2 pages.
Costunchenok B M., et al., "Effect of Vacuum on Surgical Purulent Wounds," Vestnik Chirurgia, Sep. 1986, 6 pages.
Davydov Y A., et al., "Concepts for Clinical Biological Management of the Wound Process in the Treatment of Purulent Wounds Using Vacuum Therapy," Vestnik Khirurgii, Feb. 1991, pp. 15-17.
Davydov Y. et al., "Vacuum Therapy in the Treatment of Purulent Lactation Mastitis," Russian Journal: Vesnik Khirurgii, Sep. 1986, pp. 66-70.
Davydov Y.A., et al., "Pathogenic Mechanisms of the Effect of Vacuum Therapy on the Course of the Wound Process," Khirurgiya, vol. 6, Dec. 1990, pp. 42-47.
Davydov Y.A., et al., "The Bacteriological and Cytological Assessment of Vacuum Therapy of Purulent Wounds," Vestnik Khirurgii, Oct. 1988, pp. 11-14.
De Lange M.Y., et al., "Vacuum-Assisted Closure: Indications and Clinical Experience," Eur J Plast Surg (2000), vol. 23, Feb. 9, 2000, pp. 178-182.
Decision of Rejection for Japanese Patent Application No. 2006537411, mailed on Dec. 15, 2009, 2 pages.
Dilmaghani A., et al., "A Method for Closed Irrigation and Suction Therapy in Deep Wound Infections," Journal of Bone and Joint Surgery, Mar. 1969, vol. 51-A(2), pp. 323-342.
Extended European Search Report for Application No. 12789546.4, mailed on Dec. 5, 2014, 4 pages.
Fleischmann W., et al., "Vacuum Sealing: Indication, Technique, and Results," Eur J Orthop Surg Traumatol, vol. 5, 1995, pp. 37-40.
Fleischmann W., "Vakuumversiegelung zur Behandlung von Problemwunden" Wund Forum Spezial, (with English translation: Vacuum Sealing for Treatment of Problematical Wounds), IHW '94, pp. 54-55 (6 pages with English translation).
Garcia-Rinaldi R., et al., "Improving the Efficiency of Wound Drainage Catheters," American Journal of Surgery, Sep. 1975, vol. 130, pp. 372-373.
Hartz R.S., et al., "Healing of the Perineal Wound," The Archives of Surgery, Apr. 1980, vol. 115, pp. 471-474.
Health Technology Literature Review, "Vacuum Assisted Closure Therapy for Wound Care," The Medical Advisory Secretariat, Dec. 2004, pp. 1-57.
International Preliminary Report on Patentability for Application No. PCT/GB2004/004549, mailed on Dec. 20, 2005, 7 pages.
International Preliminary Report on Patentability for Application No. PCT/US2012/039103, mailed on Nov. 26, 2013, 7 pages.
International Search Report for Application No. PCT/GB2004/004549, mailed on Feb. 21, 2005, 4 pages.
International Search Report for Application No. PCT/US2012/039103, mailed on Sep. 6, 2012, 3 pages.
Japanese Office Action dated Jun. 22, 2010 for Patent Application No. JP20060537411, 10 pages.
Jeter K F., et al., "Managing Draining Wounds and Fistulae: New and Established Methods," Chronic Wound Care, Chapter 27, 1990, pp. 240-246.
Johnson F.E., "An Improved Technique for Skin Graft Placement using a Suction Drain, Surgery, Gynecology and Obstetrics," Dec. 1984, pp. 584-585 (3 pages).
KCI Inc., "If It's not V.A.C. Therapy, It's not Negative Pressure Wound Therapy," KCI Brochure, Jan. 2005, 5 pages.
Khirugii V., "A Collection of Published Studies Complementing the Research and Innovation of Wound Care," The Kremlin Papers, Perspectives in Wound Care, Russian Medical Journal, Blue Sky Publishing, 2004, pp. 2-17.
Kostiuchenok B.M., et al., "The Vacuum Effect in the Surgical Treatment of Purulent Wounds," Russian Journal: Vestnik Khirurgii, Sep. 1986, pp. 18-21.
Landes R.R., et al., "An Improved Suction Device for Draining Wounds," Arch. Surg., vol. 104, May 1972, p. 707.

(56) References Cited

OTHER PUBLICATIONS

Linden, W.V.D., et al., "Randomized Trial of Drainage After Cholecystectomy: Suction Versus Static Drainage Through a Main Wound Versus a Stab Incision," American Journal of Surgery, Feb. 1981, vol. 141, pp. 289-294.
McFarlane R.M., "The Use of Continuous Suction under Skin Flaps," British Journal of Plastic Surgery, 1958, pp. 77-86.
McLaughlan J., et al., "Sterile Microenvironment for Postoperative Wound Care," The Lancet, Sep. 2, 1978, pp. 503-504.
Meyer D.C., et al., "Weight-Loaded Syringes as a Simple and Cheap Alternative to Pumps for Vacuum-Enhanced Wound Healing," Plastic and Reconstructive Surgery, Jun. 2005, vol. 115(7), pp. 2174-2176.
Meyer W., et al., "In Surgery, Medicine and the Specialties a Manual of its Practical Application", Bier's Hyperemic Treatment, W.B. Saunders Company, 1908, pp. 44-65.
Morykwas M.J., et al., "Vacuum-Assisted Closure: A New Method for Wound Control and Treatment: Animal Studies and Basic Foundation," Annals Plastic Surgery, vol. 38 (6), Jun. 1997, pp. 553-562.
Nakayama Y., et al., "A New Method for the Dressing of Free Skin Grafts," Plastic and Reconstructive Surgery, vol. 86(6), Dec. 1990, pp. 1216-1219.
Notice of Reasons for Rejection for Japanese Patent Application No. 2006537411, mailed on Aug. 25, 2009, 4 pages.
Notice of Reasons for Rejection for Japanese Patent Application No. 201059188, mailed on Jan. 17, 2012, 2 pages.
Nursing75., "Wound Suction: Better Drainage with Fewer Problems," vol. 5(10), Oct. 1975, pp. 52-55.
Office Action mailed Jul. 17, 2015 for Chinese Application No. 201280036812.0, 9 pages.
Office Action mailed Aug. 22, 2011 for Canadian Application No. 2739605, 2 pages.
Office Action mailed Aug. 29, 2008 for Chinese Application No. 200480032101.1, 10 pages.
Ramirez O.M., et al., "Optimal Wound Healing Under Op-Site Dressing," Ideas and Innovations, vol. 73 (3), May 9, 1983, pp. 474-475.
Ranson, J.H.C., et al., "Safer Intraperitoneal Sump Drainage," Surgery, Gynecology & Obstetrics, Nov. 1973, vol. 137, pp. 841-842.
Sames C.P., "Sealing of Wounds with Vacuum Drainage", British Medical Journal, Nov. 5, 1977, p. 1223.
Solovev V. A, et al., "The Method of Treatment of Immature External Fistulas in the Upper Gastrointestinal Tract—Guidelines," USSR Ministry of Health, S. M. Kirov Gorky State Medical Institute, 1987, 19 pages.
Solovev V.A., "Treatment and Prevention of Suture Failures after Gastric Resection," Dissertation Abstract, Gorky, 1988, 51 pages.
Stewart J., "World Wide Wounds—Next Generation of Products for Wound Management," Nov. 2002, http://www.worldwidewounds.com/2003/aprii/Stewart/Next-Generation-Products.html, 13 pages.
Svedman P., "A Dressing Allowing Continuous Treatment of a Biosurface," IRCS Medical Science: Biomedical Technology; Clinical Medicine; Surgery and Transplantation, vol. 7, 1979, p. 221.
Svedman P., et al., "A Dressing System Providing Fluid Supply and Suction Drainage Used for Continuous or Intermittent Irrigation," Annals of Plastic Surgery, vol. 17 (2), Aug. 1986, 9 pages.
Svedman P., "Irrigation Treatment of Leg Ulcers," The Lancet, Sep. 3, 1983, pp. 532-534.
Swift S., et al., "Quorum Sensing in Aeromonas Hydrophila and Aeromonas Salmoncida: Identification of LuxRI Homologs AhyRI and AsaRI and Their Cognate N-Acylhomoserine Lactone Signal Molecules," Journal of Bacteriology, Sep. 1997, vol. 179, No. 17, pp. 5271-5281.
Teder H., et al., "Continuous Wound Irrigation in the Pig," Journal of Investigative Surgery, 1990, vol. 3, pp. 399-407.
The Free Dictionary, "Flap Valve," Webster's Revised Unabridged Dictionary, retrieved from http://www.thefreedictionary.com/flapper+ valve, published 1913 by C. & G. Merriam Co, 2 pages.
Tribble D E., "An Improved Sump Drain-Irrigation Device of Simple Construction," Archives of Surgery, vol. 105, Sep. 1972, pp. 511-513.
U.S Office Action mailed on Jun. 17, 2009 for U.S. Appl. No. 10/575,875, 19 pages.
Usupov Y. N., et al., "Active Wound Drainage," Russian Journal: Vestnik Khirurgii, Apr. 1987 (p. 42-45), Perspectives in Wound Care, BlueSky Publishing, pp. 8-10.
Venturi M L., et al., "Mechanisms and Clinical Applications of the Vacuum-Assisted Closure (VAC) Device," Am J Clin Dermatol, 2005, vol. 6, No. 3, pp. 185-194.
Viljanto J., et al., "Local Hyperalimentation of Open Wounds," Br. J. Surg., vol. 63, 1976, pp. 427-430.
Wackenfors A., et al., "Effects of Vacuum-Assisted Closure Therapy on Inguinal Wound Edge Microvascular Blood Flow," Wound Repair and Regeneration, vol. 12, No. 6, Nov.-Dec. 2004, pp. 600-606.
Webb L X., "New Techniques in Wound Management: Vacuum-Assisted Wound Closure," Journal of the American Academy of Orthopaedic Surgeons, vol. 10, No. 5, Sep./Oct. 2002, pp. 303-311.
Westaby S., et al., "A Wound Irrigation Device," The Lancet, Sep. 2, 1978, pp. 503-504.
Wooding-Scott M., et al., "No Wound is Too Big for Resourceful Nurses," RN, Dec. 1988, pp. 22-25.
Written Opinion for Application No. PCT/US2012/039103, mailed on Sep. 6, 2012, 6 pages.
Wu S.H., et al., "Vacuum Therapy as an Intermediate Phase in Wound Closure: A Clinical Experience," Eur J Plast Surg, 2000, vol. 23, pp. 174-177.

METHOD AND APPARATUS FOR PROVIDING NEGATIVE PRESSURE TO A NEGATIVE PRESSURE WOUND THERAPY BANDAGE

CROSS REFERENCE TO RELATED APPLICATIONS

This application is a continuation of U.S. patent application Ser. No. 16/234,241, filed Dec. 27, 2018, which is a continuation of U.S. patent application Ser. No. 14/737,387, filed Jun. 11, 2015 and issued as U.S. Pat. No. 10,300,178, which is a continuation of U.S. patent application Ser. No. 13/299,783, filed Nov. 18, 2011 and issued as U.S. Pat. No. 9,067,003, titled "METHOD FOR PROVIDING NEGATIVE PRESSURE TO A NEGATIVE PRESSURE WOUND THERAPY BANDAGE," which claims priority to U.S. Provisional Application No. 61/490,118, filed May 26, 2011, titled "METHOD FOR PROVIDING NEGATIVE PRESSURE TO A NEGATIVE PRESSURE WOUND THERAPY BANDAGE." The disclosure of each of these prior applications is hereby incorporated by reference in its entirety herein.

FIELD OF THE INVENTION

The invention relates to a method for providing negative pressure to a negative pressure wound therapy bandage.

BACKGROUND OF THE INVENTION

Negative pressure wound therapy is one method that is used to treat certain wounds or sores on people. In general the treatment includes, a bandage being placed over a wound site, and connected to a pumping device. The pumping device provides suction, creating a negative pressure under the bandage at the wound site. Exudates and other materials are removed from the wound site, allowing the wound to heal faster than under ambient pressure.

The pumping device includes, amongst other things, a pump. Typically, a user selects (or otherwise enters) an appropriate therapeutic pressure on the pumping device that correlates to the specific negative pressure treatment for that patient. It is important that the pump and pumping device achieve the therapeutic pressure that is to be used in association with the negative pressure wound therapy quickly and correctly.

The speed at which the pump can achieve the therapeutic pressure is important because the speed can detrimentally effect the treatment. Moreover, the ability for the pump to recognize that the therapeutic pressure has been achieved is important to avoid applying too little or too much negative pressure. Thus, for a pump device, the speed and the accuracy at which it obtains the therapeutic pressure is an important characteristic.

In order to accurately and quickly achieve the therapeutic pressure, some pumps are left on continuously. In some devices this can be problematic. For example, some pumps can quickly achieve the therapeutic pressure; however, the pump and system tends to overshoot the therapeutic pressure value. This requires additional valves and other components that allow the pumping device to release negative pressure until the appropriate negative pressure is obtained.

Moreover, leaving the pump on continuously can act as a power drain, and for pumping devices that operate on batteries or other portable power sources, this can negatively impact the life time of the power source.

The present invention is directed to resolving these and other matters.

SUMMARY OF THE INVENTION

In one embodiment of the invention, the invention is directed towards a method for providing negative pressure to a negative pressure wound therapy bandage by providing a pumping device having a pump and setting a therapeutic negative pressure on the pumping device. The pumping device determines a target negative pressure associated with the therapeutic negative pressure and the target negative pressure is less than the therapeutic negative pressure (as discussed herein, "less than" means it is less negative, or a lower amount of a negative pressure, in other words, closer to zero). The pumping device is connected to a negative pressure wound therapy bandage. The target negative pressure is achieved by cycling the pump on and off to create a negative pressure in the negative pressure wound therapy bandage, obtaining a plurality of samples of the negative pressure in the negative pressure wound therapy bandage, each sample being obtained at a first set time interval, calculating an average of a predetermined number of consecutive samples, comparing the average to the target negative pressure, and, continuing to cycle the pump on and off until the average is greater than the target pressure.

The method may also include after cycling the pump on and off until the average of samples is greater than the target pressure after the complete off cycle, sampling the negative pressure in the negative pressure wound therapy bandage at a second set time interval greater than the first set time interval.

In another embodiment of the invention, the sampling of the negative pressure in the negative pressure wound therapy bandage at the second set time interval begins when the pump has been off for a predetermined amount of time.

The predetermined amount of time may be 300 milliseconds.

The second set time interval may be 1000 milliseconds and the first set time interval is 100 milliseconds.

In an embodiment, the cycling of the pump on and off to create negative pressure in the negative pressure wound therapy bandage on is performed by turning the pump on for 80 milliseconds and then turning the pump off for 80 milliseconds.

In some embodiments of the present invention, the therapeutic negative pressure is 125 mmHg and the target negative pressure is approximately 115 mmHg.

In some embodiments of the present invention, the therapeutic negative pressure is 90 mmHg and the target negative pressure is approximately 85 mmHg.

In some embodiments of the present invention, the therapeutic negative pressure is 60 mmHg and the target negative pressure is approximately 54 mmHg.

In some embodiments of the present invention, the therapeutic negative pressure is 40 mmHg and the target negative pressure is approximately 34 mmHg.

In another embodiment of the invention, the invention is for a method for providing negative pressure to a negative pressure wound therapy bandage by providing a pumping device having a pump and setting a therapeutic negative pressure on the pumping device. The pumping device determines a target negative pressure associated with the therapeutic negative pressure and the target negative pressure is less than the therapeutic negative pressure. The pumping device is connected to a negative pressure wound therapy bandage. The target negative pressure is achieved by cycling the pump on and off for a first predetermined amount of time to create a negative pressure in the negative pressure wound therapy bandage, obtaining a plurality of samples of the negative pressure in the negative pressure wound therapy bandage, each sample being obtained at a first set time interval, calculating an average of a predetermined number of consecutive samples, comparing the average to the target negative pressure, and, if the average is not greater than the target negative pressure, repeating the steps of cycling the pump on and off, obtaining a plurality of samples, calculating an average and comparing the average, until the average is greater than the target negative pressure.

In some embodiments the comparing of the average occurs at a rate faster than the rate of calculating the average.

In some embodiments, if the average is greater than the target negative pressure, the target negative pressure is maintained by obtaining a plurality of second samples of the negative pressure in the negative pressure wound therapy bandage at a second set time interval begin greater than the first time interval, and, comparing each second sample to the target negative pressure, and, repeating the steps of obtaining and comparing if a second sample is greater than the target negative pressure.

In some embodiments, if a second sample is not greater than the target negative pressure, the step of achieving the target negative pressure by: cycling the pump on and off; obtaining a plurality of samples; calculating an average; and, comparing the average until the average is greater than the target negative pressure, is repeated.

In the various embodiments of the present invention, the therapeutic negative pressure may be selected from the group consisting of: 40 mmHg; 60 mmHg; 90 mmHg; and, 125 mmHg.

An invention according to one or more of the disclosed embodiments allows the pump to achieve the therapeutic negative pressure/target negative pressure reasonably quickly and limit exceeding the therapeutic negative pressure/target negative pressure as much as practical.

Moreover, at least one of the embodiments also provides a reliable method to detect when the bandage pressure was being "topped-up" too frequently due to a leak (i.e., often returning to cycle the pump on and off to increase negative pressure). It is expected that the system will leak a small amount over time, for example, due to the imperfect plumbing connections in the system. A leak rate of one "top-up" per minute is normal. However, a leak rate four times that is cause for a minor leak to be declared. Such a leak rate is still within the bounds of the system to handle long term but the user should be informed so that it is corrected and system battery life is extended. It is also desirable to clear the fault as soon as it appears that the leaking has returned to normal levels.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

The present invention will become more fully apparent from the following description and appended claims, taken in conjunction with the accompanying drawings. Understanding that the accompanying drawings depict only typical embodiments, and are, therefore, not to be considered to be limiting of the scope of the present disclosure, the embodiments will be described and explained with specificity and detail in reference to the accompanying drawings as provided below.

DETAILED DESCRIPTION OF THE DRAWINGS

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

Reference throughout this description to features, advantages, objects or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Figure 1:
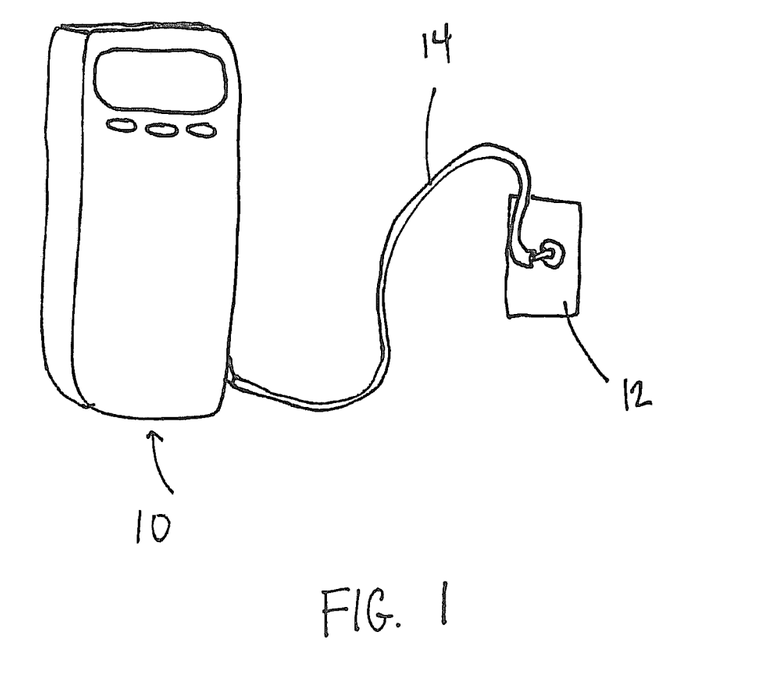
FIG. 1 is a front perspective view of a device used in association with one or more embodiments of the present invention.
Figure 2:
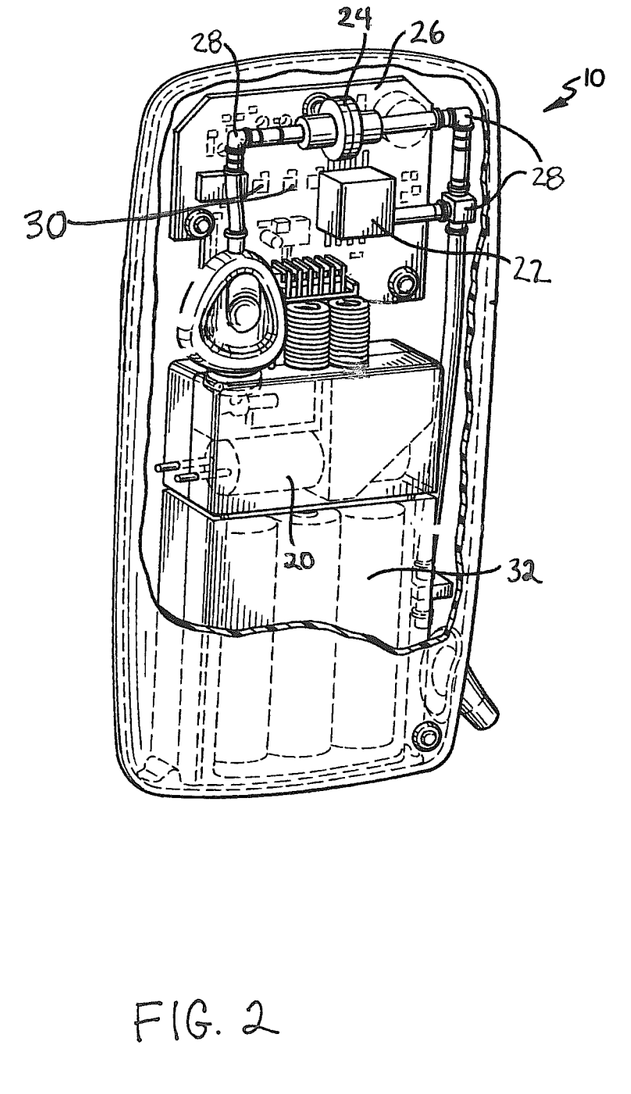
FIG. 2 is a front side cutaway view of a device provided according to one or more embodiments of the present invention.

As shown in the attached FIGS. 1 and 2, the present invention is directed towards a method used with a pumping device 10 having a pump 20. The pumping device 10 generally includes a pressure sensor 22, a check valve 24, a control circuit 26 (with microcontroller), internal plumbing 28, LEDs 30 and a power source 32.

In order to provide negative pressure to a wound, the pumping device 10 is connected to a negative pressure wound therapy bandage 12, typically with tubing 14.

In order to achieve a target negative pressure the pumping device 10 turns the pump 20 on for short amounts of time when the pressure is below the target pressure.

The pump device 10 typically operates as follows: a microcontroller turns the pump 20 on via a digital output; the pump 20 starts producing a vacuum; the vacuum is converted to a voltage by a pressure sensor 22; the voltage is converted by an analog to digital converter ("the A/D") to a standard, recognized pressure engineering unit; and, the microcontroller compares the monitored pressure to the target pressure.

In order to achieve the target negative pressure in a short amount of time and avoid overshooting the target negative pressure, the pump 20 is cycled. The duty cycle, the percentage of pump on time relative to pump off time, after examining several pumps in action, can be constant for a variety of pumps 20. How much vacuum the pump 20 can draw in a short time period will influence the pump on time. Moreover, bandage 14 and plumbing 28 elasticity and how quickly the pressure sensor 22 and the A/D can take a measurement will influence the pump off time.

In one embodiment, the pressure sensor 22 measurement time is 20 milliseconds; while the A/D measurement time is 16 microseconds. Therefore, since a change in pressure must first be converted by the pressure sensor 22 and then the A/D, the minimum measurement time is 20.016 milliseconds.

It is believed to be advantageous to average readings before they are used to mitigate occasional measurement system anomalies. The number of samples in the average, on the one hand, when it tends to be low, do some anomaly mitigation but also remain the most responsive to quick changes in the parameter they are measuring. The best anomaly mitigation appears to occur when the number of samples is high, but then the averaging is not very responsive to quick changes in the parameter they are measuring.

It was determined that it would be advantageous to use a sliding 5 sample average. If the pressure were sampled continuously, a complete average would be ready in: 5×20.016=100.090 milliseconds. However, it would not be necessary to wait for all 5 samples to be acquired before a pump control decision was made on the value because just a few samples still mitigates against system anomalies sufficiently. However, sampling the pressure continuously, especially since the pressure sensor 22 places the largest mA load of any component (other than the pump 20) on the system would unnecessarily shorten battery life for too little gain in pump control.

Consequently, a measurement process asynchronous to the pump on/off cycle was used wherein pressure samples are contributed to the average every 100 milliseconds, and if the pump on/off control logic compared the average every 80 milliseconds it would compare it often enough to determine an average affected by the very last contribution that was made to that average. This can be achieved by: starting the process every 100 milliseconds; waiting the 20 milliseconds pressure sensor measurement time; then, measuring the pressure with the A/D.

It is contemplated to synchronize the completion of the A/D measurement to the pump on/off control logic exactly but software design best practice says that dependencies between software modules should be avoided where possible and synchronization is not necessary here—the pump on/off control logic (cycle) will see every change any contribution makes to the average.

When the pump 20 has met its target pressure, the A/D sampling and comparing process detailed above changes from, for example, a repeat rate of 100 milliseconds to a repeat rate of 1000 milliseconds when the pump has been off for a sufficient amount of time. This further saves battery life at a time when the pressure is not likely to change very much. The period of time the pump 20 has to be off to switch to the slower repeat rate may be, for example, 300 milliseconds; however, it may be any value that was larger than the off period in the pump on/off duty cycle (more later on the duty cycle). Moreover, it should be at least that long to distinguish the "off" that is due to the pump 20 having reached the target pressure and the "off" of the pump control duty cycle. (The 300 milliseconds was utilized as it is a sufficient amount of time for the A/D to wait before it samples the battery voltage after the pump is turned off. The battery is only sampled when the pump 20 is turned off because the mA load that the pump places on the system is significantly different than when it is off and battery life is more easily predicted when the pump is not loading the system.)

The pump control on/off duty cycle is preferably 80 milliseconds on and 80 milliseconds off. It was determined that an "on" time of 40 or 80 milliseconds was sufficient for constraining the overshoot for a variety of bandages 12. The 40 milliseconds value constrained it better, yielded end pressures closer to the target pressure, but took longer to get to the target pressure. The "on" times longer than 80 milliseconds created out-of-bounds overshoot for some bandages—no matter what the "off" time was. As mentioned above, the "off" time has an effect on the measurement part of the control/measurement algorithm. Further, plumbing and bandage elasticity, although minor, can contort the average or "steady" pressure for a short while. It is believed that it is advantageous to let such pressure contortions settle before measurement. Moreover, the pressure sensor 22 and A/D measurements need time also as noted above.

An "off" time of approximately 30 milliseconds would cover both but it was convenient to use the same 80 milliseconds timer to control both the on time and the off time. Further, letting the system settle longer, for one or more multiples of the 80 milliseconds, would improve the quality of the measurement because it would let the sliding average fill more completely—at the cost of taking longer to get to the end pressure. While these times have been discussed, nothing herein should be construed to limit the present invention to these times.

In use, a user inputs the therapeutic negative pressure into the pumping device. Of course, this can be accomplished with the pumping device having pre-set therapeutic negative pressures and the user merely selects one.

In one or more embodiments of the present invention, a target negative pressure is set slightly less than the therapeutic negative pressure entered by the user into pumping device. In a working example of an embodiment of the invention, the following parameters were used with the object to obtain the therapeutic negative pressure of 40/60/90/125 mmHg within 15 seconds and limit overshoot to +/−10% of the therapeutic negative pressure. However, for the 40 mmHg therapeutic negative pressure, the tolerance is preferably +/−10 mmHg (not +/−10%).

Using a target negative pressure that is set slightly less than the 40/60/90/125 therapeutic negative pressure allows for compensation of the system's tendency to undervalue the actual negative pressure within the bandage. Therefore, the target pressures contemplated to be used with the previously mentioned therapeutic negative pressure values are 34, 54, 85 and 115 mmHg (respectively). Other target pressures can be used depending on the variety of parameters discussed above (pump, bandage, elasticity, etc.) without departing from the spirit of the present invention.

In a device according to one or more embodiments of the present invention, the pump 20 will reasonably quickly achieve the target negative pressure, stop, "top-up" once or twice after a few seconds and transition to the state where it only tops-up every minute or so to compensate for system leaking. The initial one or two top-ups are due to the pressure completely settling.

In sum, in one or more embodiments of the present invention, pressure is sampled every 100 ms; with the sampling by the pressure sensor and A/D taking 20.016 milliseconds. Samples go into a sliding 5 element average. The pumping device 10 asynchronously compares the average every 80 milliseconds s (slightly faster than the pressure is sampled). The pumping device 10 turns the pump 20 on for no more than one cycle (80 milliseconds) if pressure is below target pressure. After waiting one off cycle (80 milliseconds), if the pressure is still below the target pressure, the pump 20 is turned on again. These last two steps repeat until the pressure is greater than the target pressure, at which point the pump 20 is left off until the normal leaking in the system reduces the pressure below the target pressure. During the period when the pressure is above the target pressure, starting when the pump 20 has been continuously off for 300 milliseconds, sampling may be reduced to the 1000 milliseconds rate (to extend battery life).

Figure 3:
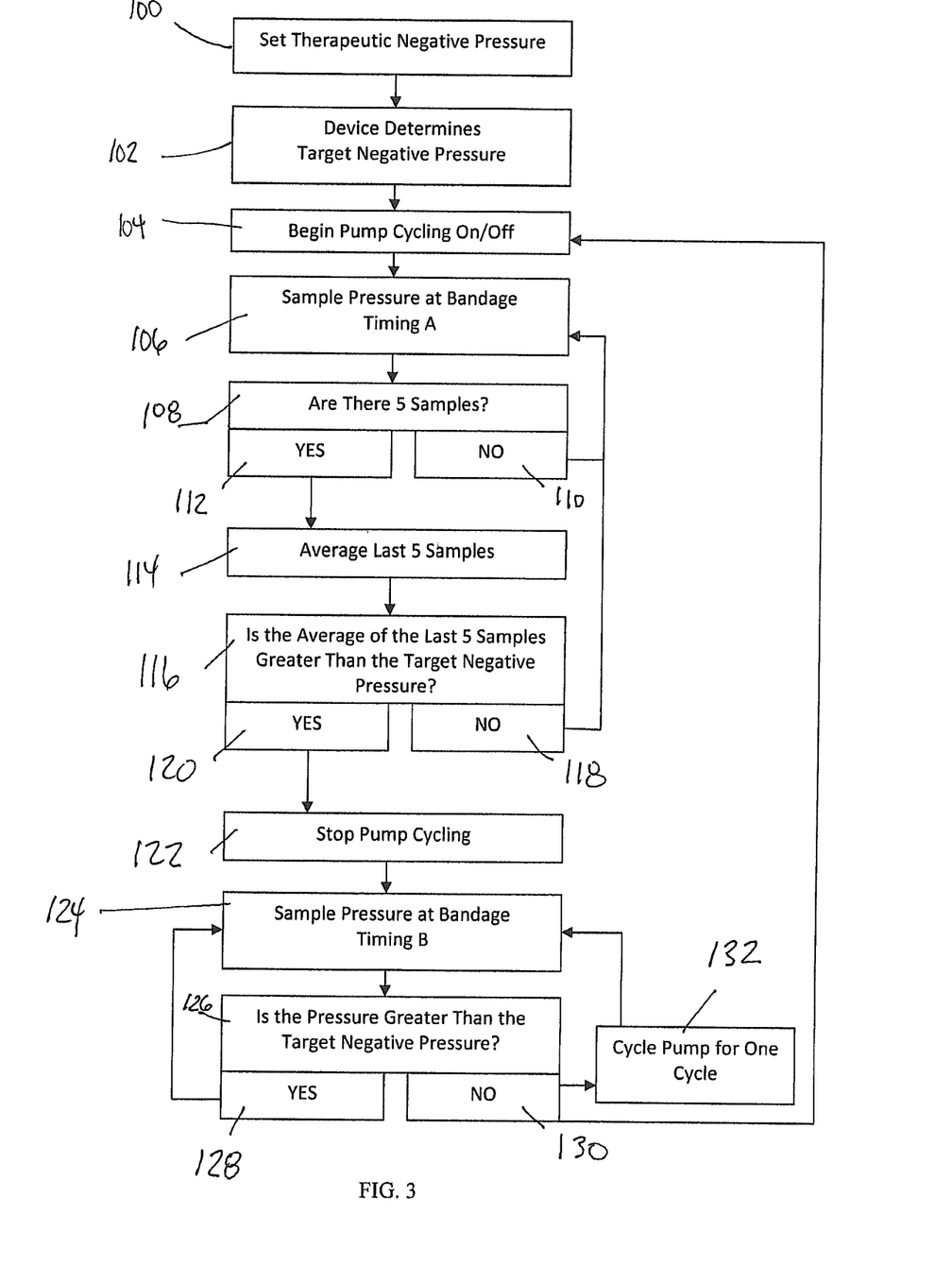
FIG. 3 is a flow chart of a method according to one or more embodiments of the present invention.

A flow chart for performing the steps of some embodiments is shown in FIG. 3. As shown therein, and as discussed above, a method according to one or more embodiments of the present invention may begin with the setting of a therapeutic negative pressure 100. In response to same, the pumping device will determine a target negative pressure 102. As previously discussed the target negative pressure is less than the therapeutic negative pressure.

At this point, the pumping device will begin to cycle the pump on and off 104. In addition, the pumping device will also begin sampling the pressure at the bandage 106. This sampling is preferably done at a set time. In FIG. 3, this is shown as being at "Timing A." The pumping device determines if there are at least five samples measured 108. If less than five samples have been collected 100, the pumping device continues to sample the pressure at the bandage 106.

If, however, more than five samples have been collected 112, the pumping device will calculate the average of the last five samples taken 114. The pumping device will then compare the average of the last five samples to the target negative pressure 116. If the average of the last five samples is less than the target negative pressure 118, the pumping device will continue to sample the pressure at the bandage 106.

If the average of the last five samples is greater than the target pressure 120, the pumping device will cease the pump cycling. It is contemplated, although not required, that if the pump is in the middle of a cycle, that specific cycle be completed, before the pumping cycling is stopped. Alternatively, the pump cycling can be immediately stopped when the average is determined to be greater than the target negative pressure.

After the pump cycling has been stopped, the device begins sampling the pressure at the bandage 124. This sampling is conducted, preferably at a predetermined time interval, and as shown, occurs at "Timing B." As previously mentioned, in order to increase the life of the batteries that may be powering the pumping device, it is preferred that Timing B is greater than Timing A.

Finally, the device continues to compare the sample of the pressure (taken in step 124) with the target negative pressure 126. If the most recent sample is greater than the target negative pressure 128, the device continues to sampling the pressure at the bandage 124.

If the most recent sample is less than the target pressure 130, the device may turn the pump on for one cycle 132, and continue to sample the pressure under the bandage 124. Alternatively, the device can return to cycling the pumping on and off 104 and the subsequent steps previously taken to achieve the target negative pressure.

In addition to achieving and maintaining negative pressure, one or more embodiments of the present invention also include a method for detecting a leak. For example, if the target negative pressure has been reached and at least 20 top-ups have occurred at the target negative pressure and the average of the last N (=3) top-up intervals is less than 15 seconds, a leak may be declared by the pump device. The minor leak detection may be cleared if the pump is disabled by the user or the top-up intervals are greater than or equal to 15 seconds.

The 15 seconds time value is related to an unacceptable leak rate (4 top-ups per minute) that was determined to be optimal. The pumping device records the time (since unit reset) of every top-up into a circular array of N elements and checks the top-up interval at every top-up or every 80 milliseconds, whichever occurs first. (The "or 80 milliseconds" facet is more useful for clearing the fault than declaring it.)

The time in the oldest of the array elements is subtracted from the current time and then divided by N to either yield the average of the last N top-ups (or what the average would have been if the 80 milliseconds timer tick that prompted the check was a top-up). An example of setting the fault and clearing the fault is given below:

TABLE ONE

Setting the fault (assume 17 top-ups for this pressure have already occurred):

| Top-Up # | Time | Note |
| --- | --- | --- |
| 18 | 05:42:23.000 | |
| 19 | 05:42:33.000 | |
| 20 | 05:42:43.000 | Check called due to this top-up. System time is 05:42:43. System time − oldest top-up time = 00:00:20 00:00:20/3 = 6 6 < 15, fault declared |

The checks called due to the 80 milliseconds timer expiring are not shown in the above because they would have had no effect and their omission makes it easier to understand how the checks due to just the top-ups take place.

TABLE TWO

Clearing the fault (assume a continuation of the above TABLE ONE)

| Top-Up # | Time | Note |
| --- | --- | --- |
| 18 | 05:42:23.000 | |
| 19 | 05:42:33.000 | |
| 20 | 05:42:43.000 | Check called due to this top-up. System time is 05:42:43. System time − oldest top-up time = 00:00:20 00:00:20/3 = 6 6 < 15, fault declared |
| | 05:42:43.080 | Check called due to 80 ms timer tick, System time is 05:42:43.080 System time − oldest top-up time = 00:00:20.080 00:00:20.080/3 = 6 6 still less than 15, fault stands |
| | 05:42:43.160 | Similar to the previous, fault stands |
| | etc | No top-ups |
| | etc | No top-ups |
| | 05:43:08.000 | Check called due to 80 ms timer tick System time is 05:43:08.000 System time − oldest top-up time = 00:00:45 00:00:45/3 = 15 15 is not less than 15, fault cleared. |

In the example above, the fault was cleared within 25 seconds of the last top-up, a fraction of three times the 15 seconds threshold (the threshold used to declare the fault). This is consistent with the goal of clearing the fault quickly if it appears as though the fault has been corrected. It could have been cleared even sooner, as fast as within 15 seconds, if the system time was compared to the newest recorded top-up instead of the oldest—but using more than one top-up time gives greater confidence that the fault has really been cleared.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

What is claimed is:

1. A method of operating a negative pressure wound therapy device, the method comprising, by a controller of the negative pressure wound therapy device:
operating a source of negative pressure of the negative pressure wound therapy device in a first mode to provide negative pressure to a wound covered by a wound dressing, the source of negative pressure configured to be fluidically connected to the wound;
determining pressure at the wound;
comparing the pressure at the wound to a target negative pressure;
at a first time:
determining that the target negative pressure has not been established at the wound; and
in response to determining that the target negative pressure has not been established at the wound, continue operating the source of negative pressure in the first mode;
at a second time:
determining that the target negative pressure has been established at the wound; and
in response to determining that the target negative pressure has been established at the wound, operating the source of negative pressure in a second mode in which less power is consumed than in the first mode,
wherein operating the source of negative pressure in the second mode comprises cycling the source of negative pressure on and off to maintain the target negative pressure at the wound, and
wherein the source of negative pressure does not provide negative pressure to the wound when the source of negative pressure is off; and
indicating a presence of a leak in response to determining that a duration of time during which the source of negative pressure has been activated over a time period satisfies a threshold indicative of a leak,
wherein determining the pressure at the wound comprises:
in the first mode, determining the pressure at the wound at a first sampling rate, and
in the second mode, determining the pressure at the wound at a second sampling rate lower than the first sampling rate.

2. The method of claim 1, further comprising, in the second mode:
determining that the pressure at the wound is more positive than the target negative pressure; and
in response to determining that the pressure at the wound is more positive than the target negative pressure, activating the source of negative pressure to provide negative pressure to the wound.

3. The method of claim 2, further comprising activating the source of negative pressure for one cycle.

4. The method of claim 1, wherein determining the pressure at the wound comprises averaging a plurality of pressures at the wound.

5. The method of claim 4, wherein comparing the pressure at the wound to the target negative pressure comprises comparing the averaged pressure to the target negative pressure.

6. The method of claim 1, wherein the target negative pressure is between −40 mmHg to −125 mmHg.

7. The method of claim 1, wherein determining the pressure at the wound is performed asynchronously with operation of the source of negative pressure.

8. A negative pressure wound therapy apparatus comprising:
a source of negative pressure configured to provide negative pressure to a wound covered by a wound dressing, the source of negative pressure configured to be fluidically connected to the wound;
a pressure sensor configured to monitor pressure; and
a controller configured to:
operate the source of negative pressure in a first mode;
determine pressure at the wound based on one or more readings of the pressure obtained by the pressure sensor;
compare the pressure at the wound to a target negative pressure;
in response to determining that the target negative pressure has not been established at the wound, continue operating the source of negative pressure in the first mode;
in response to determining that the target negative pressure has been established at the wound, operate the source of negative pressure in a second mode in which less power is consumed than in the first mode, wherein operating the source of negative pressure in the second mode comprises cycling the source of negative pressure on and off to maintain the target negative pressure at the wound, and wherein the source of negative pressure does not provide negative pressure to the wound when the source of negative pressure is off; and
indicate a presence of a leak in response to determining that a duration of time during which the source of negative pressure has been activated over a time period satisfies a threshold indicative of a leak,
wherein in the first mode, the controller is configured to determine the pressure at the wound by causing the pressure sensor to monitor pressure at a first sampling rate, and
wherein in the second mode, the controller is configured to determine the pressure at the wound by causing the pressure sensor to monitor pressure at a second sampling rate lower than the first sampling rate.

9. The apparatus of claim 8, wherein the controller is further configured to:
in response to determining that the pressure at the wound is more positive than the target negative pressure in the second mode, activate the source of negative pressure to provide negative pressure to the wound.

10. The apparatus of claim 9, wherein the controller is further configured to: activate the source of negative pressure for one cycle.

11. The apparatus of claim 8, wherein the controller is further configured to:
determine the pressure at the wound by averaging a plurality of readings of the pressure at the wound obtained by the pressure sensor.

12. The apparatus of claim 11, wherein comparing the pressure at the wound to the target negative pressure comprises comparing the averaged pressure to the target negative pressure.

13. The apparatus of claim 8, wherein the target negative pressure is between −40 mmHg to −125 mmHg.

14. The apparatus of claim 8, wherein the controller is configured to determine the pressure at the wound asynchronously with operation of the source of negative pressure.

\* \* \* \* \*